United States Patent [19]

Murakami

[11] Patent Number: 5,387,210
[45] Date of Patent: Feb. 7, 1995

[54] SANITARY NAPKIN

[75] Inventor: Masaki Murakami, Kawanoe, Japan

[73] Assignee: Uni-Charm Co., Ltd., Ehime, Japan

[21] Appl. No.: 859,739

[22] Filed: Jun. 15, 1992

[51] Int. Cl.⁶ .................. A61F 13/15; A61F 13/20
[52] U.S. Cl. ......................... 604/396; 604/385.1;
                                        604/393; 604/387
[58] Field of Search ............ 604/358, 385.1–397

[56] References Cited

U.S. PATENT DOCUMENTS

| 4,687,478 | 8/1987 | Van Tilberg | 604/387 |
| 4,695,278 | 9/1987 | Lawson | 604/385.2 |

FOREIGN PATENT DOCUMENTS 55-52758  4/1980  Japan .
58-84130  6/1983  Japan .
60-75058  4/1985  Japan .

Primary Examiner—Randall L. Green
Assistant Examiner—Rob Clarke
Attorney, Agent, or Firm—Lowe, Price, LeBlanc & Becker

[57] ABSTRACT

A sanitary napkin is provided with flaps including wings formed on laterally opposite sides thereof. Top surfaces of the flaps are formed by liquid barrier sheets of which the inner areas form together with the topsheet pockets therebetween to receive menstrual fluid. The pockets are opened as the wings are folded onto the outer sides of a crotch zone of user's underpants to fix the napkin thereto.

5 Claims, 3 Drawing Sheets

SANITARY NAPKIN

TECHNICAL FIELD OF THE INVENTION

The present invention relates to sanitary napkins (or sanitary pads) used to absorb and hold menstrual fluid and more particularly to such sanitary napkins having flaps of the wing type extending outward from laterally opposite side edges that are to be folded around a crotch zone of user's underpants and thereby to fix the napkins thereto.

BACKGROUND OF THE INVENTION

The sanitary napkins are well known which comprise a liquid-permeable topsheet, a liquid-impermeable backsheet, a liquid absorbent core sandwiched therebetween, and flaps of the wing type defined by said top- and backsheets extending outward from opposite side edges of a longitudinally central area of said core.

It is also well known to provide the sanitary napkins on opposite sides thereof with flaps each including a pocket with or without a longitudinal stretchability. Such pockets are provided to prevent menstrual fluid from leaking beyond the opposite side edges of the napkins.

However, the flaps of the former napkins certainly have a function to fix the napkins to the crotch zone of a user's underpants but no function to prevent menstrual discharge from leaking beyond the opposite side edges of the napkins. On the other hand, the flaps of the latter napkins have neither the function to wrap the crotch zone of user's underpants and thereby to fix the napkins thereto nor satisfactory function to rise during use of the napkins and thereby to serve as the pockets or barriers to hold menstrual fluid.

Accordingly, it is an object of the invention to provide novel sanitary napkins provided with the flaps of the wing type so improved to meet the above-mentioned leakage-proof function satisfactorily and reliably.

DISCLOSURE OF THE INVENTION

The present invention is premised on a sanitary napkin comprising a liquid-permeable topsheet, a liquid-impermeable backsheet, a liquid absorbent core sandwiched therebetween, and flaps including wings outwardly extending from opposite side edges of longitudinally central area of said core, at least said wings being provided on their undersides with adhesive applied thereon and is characterized in the following.

Said flaps comprise outer extensions of said backsheet extending outward from opposite outer side edges of the longitudinally central area of said core so as to define said wings, respectively, outer extensions of respective liquid barrier sheets laid upon top surfaces of respective said outer extensions of said backsheet so as to define said wings and inner areas of respective said liquid barrier sheets laid upon the top surface of said topsheet adjacent the outer side edges of said core, and that said liquid barrier sheets are bonded along their outer peripheries onto the top surface of said backsheet, on one hand, and along lines outwardly spaced from their inner side edges onto said topsheet so as to form pockets between said inner areas and said topsheet, on the other hand.

In use of such a sanitary napkin of the invention, the napkin is laid with its back side down on the inner surface of the crotch area of user's underpants, then said wings are folded onto the outer surface of said crotch area and the napkin is fixed to the crotch area by said adhesive. The inner areas lift up and the pockets are opened as the napkin is fixed to the underpants, because said inner areas of said flaps are pulled outwardly as said wings are folded onto the outer surface of said crotch area.

Menstrual fluid flowing on the top surface of the napkin toward the opposite side edges thereof is reliably received by the respective pockets and, in consequence, there is no apprehension that any quantity of menstrual fluid might leak through the opposite side edges of the napkin and stain the user's underwear.

BEST MODE FOR CARRYING OUT THE INVENTION

Figure 1:
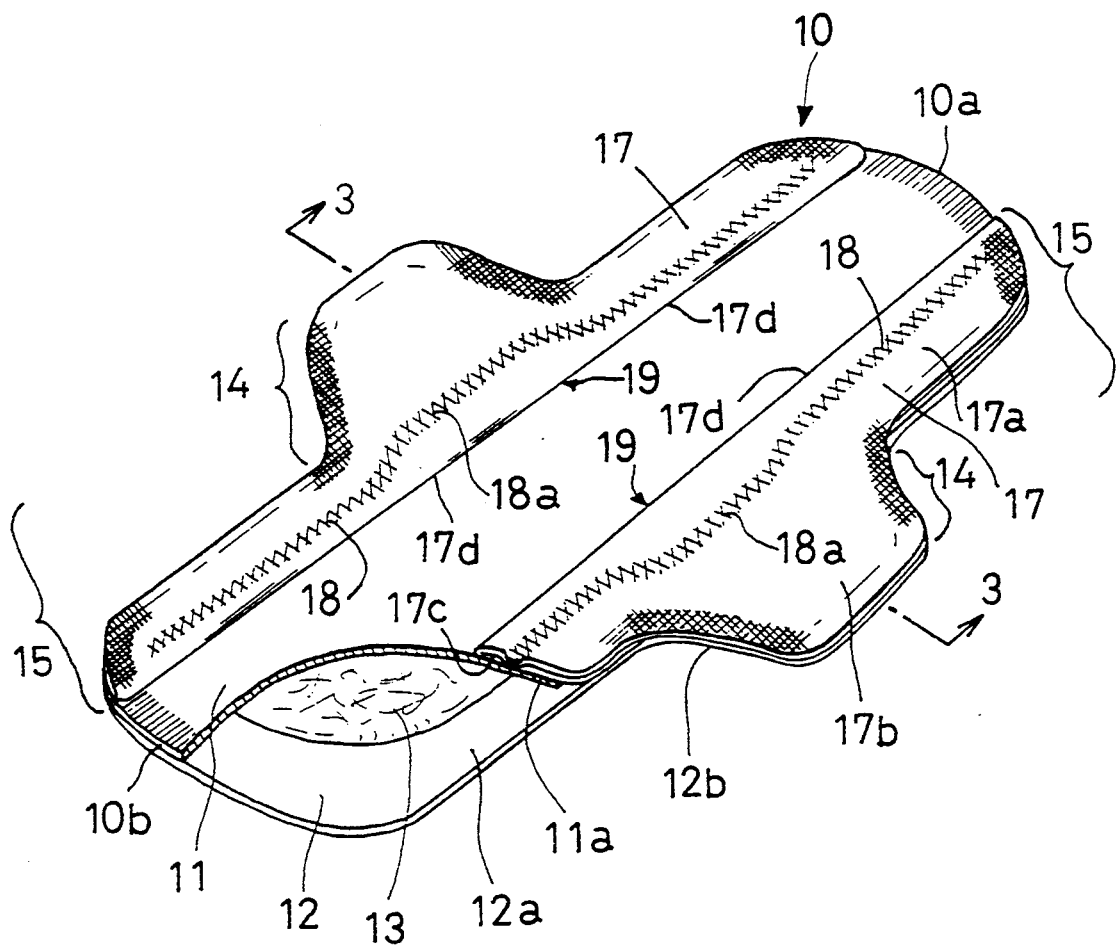
FIG. 1 is a perspective top view, partially broken away, showing an embodiment of the sanitary napkin constructed in accordance with the present invention.

The invention will be more readily understood from the following description of preferred embodiments made in reference with the attached drawings. Referring to FIG. 1, napkin 10 comprises a liquid-permeable topsheet 11, a liquid-impermeable backsheet 12, a liquid absorbent core 13 sandwiched therebetween and being dimensioned smaller than said sheets 11, 12 both in length and width so as to define peripheral outer extensions 11a, 12a of respective said sheets 11, 12 and flaps 15 including wings 14, respectively.

The backsheet 12 is dimensioned wider than the topsheet 11 so that the laterally opposite outer extensions 12a of the backsheet 12 extend outward beyond outer edges of the respective laterally outer extensions 11a of the topsheet 11. The first laterally outer extensions 11a and the associated first outer extensions 12a are bonded together by adhesive (not shown). The backsheet 12 has approximately at its longitudinally middle portion, preferably at its portion slightly put aside to a front end 10a of the napkin 10, laterally opposite second outer extensions 12b which laterally extend outward further beyond said laterally first outer extensions 12a, respectively.

Figure 5:
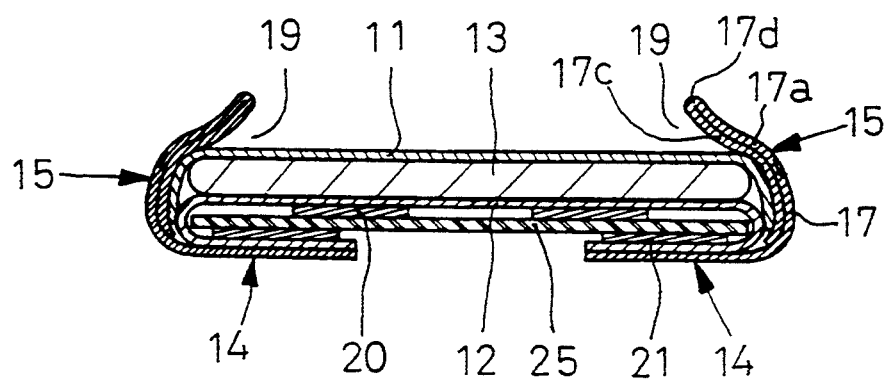
FIG. 5 is an enlarged sectional view showing the napkin of FIG. 3 as fixed to a crotch zone of user's underpants.

Laterally opposite flaps 15 each including a wing 14 comprise liquid barrier sheets 17 provided on laterally opposite sides of the napkin 10, and the first outer extensions 11a, 12a of the top- and backsheets 11, 12, respectively. More specifically, the liquid barrier sheets 17 have inner areas 17a adapted to cover the areas of the topsheet 11 lying adjacent the opposite side edges of the core 13 and the top surface of the first outer extensions 12a of the backsheet 12, outer extensions 17b adapted to cover the top surface of said second outer extensions 12b of the backsheet 12 and the turned down portions 17c. Outer edges of the liquid barrier sheets 17 are welded to the top surface of the backsheet 12 underlying them. The liquid barrier sheets 17 are also bonded under heat and pressure along the lines spaced from inner side edges 17d of the respective liquid barrier sheets 17 formed by said turning down onto the top surface of the topsheet 11 so that the bonding lines extend along the opposite side edges of the core 13 (reference numeral 18 designates these bonding lines). In this way, the bonding lines 18 and pockets 19 (FIG. 5) are formed between the inner areas 17a of the liquid barrier sheets 17 and the topsheet 11. The bonding lines 18 are preferably curved outward along the lengths across which the wings 14 are laterally opposed to each other so as to make the respective pockets 19 deeper in these areas, as shown by reference numeral 18a.

Figure 2:
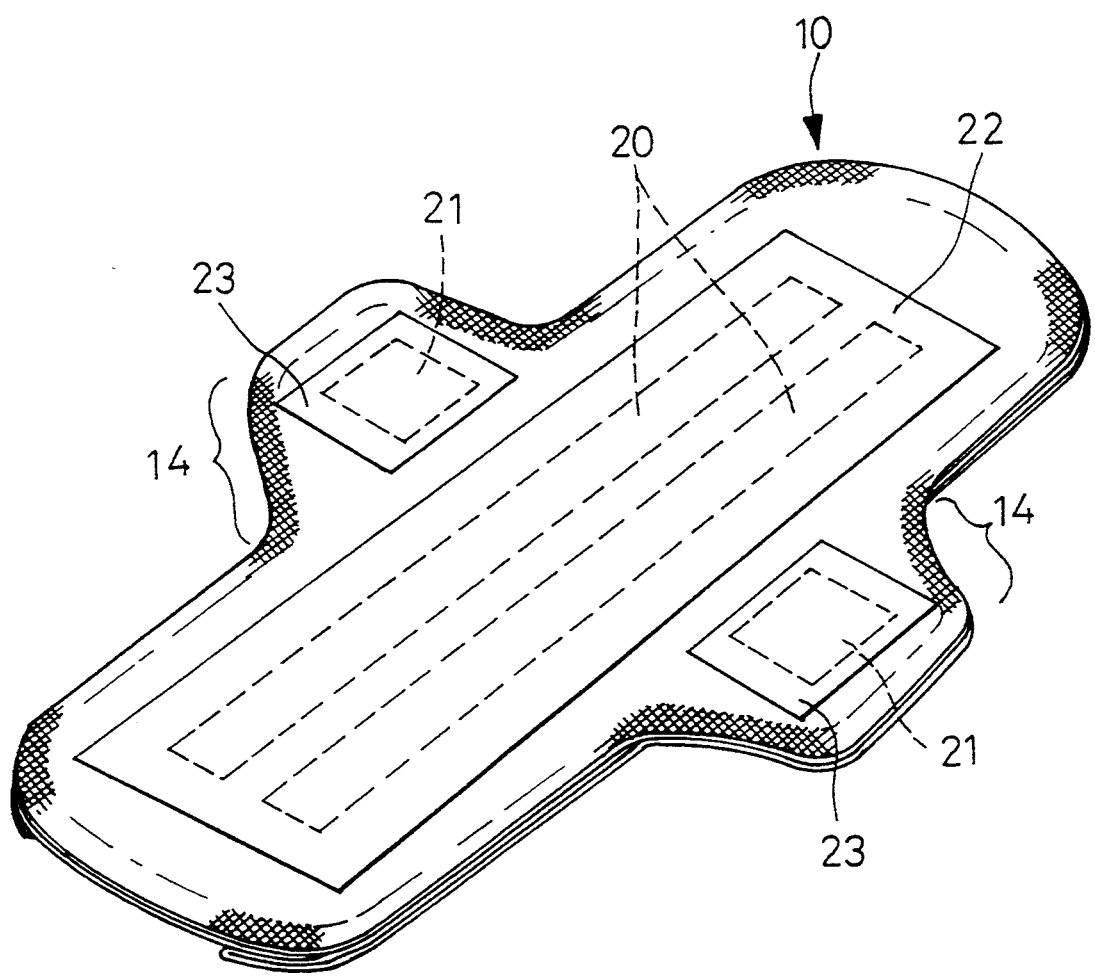
FIG. 2 is a perspective bottom view of said napkin.
Figure 3:
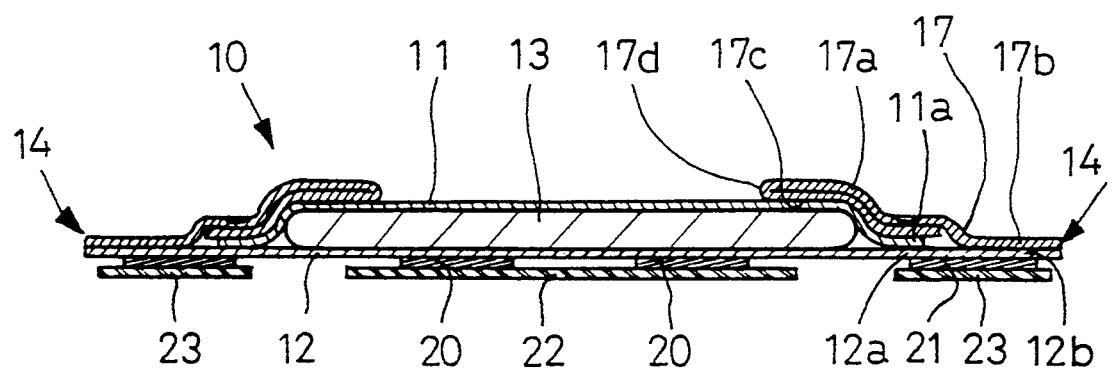
FIG. 3 is an enlarged sectional view taken along a line 3—3 in FIG. 1.

Referring to FIG. 2, the backsheet 12 centrally provided on its outer surface with adhesive 20 applied thereon in a pair of parallel strips extending longitudinally of the backsheet 12. Additionally, the respective second outer extensions 12b of the backsheet 12 are centrally provided on their outer surfaces with adhesive 21 applied squares thereon. These strips 20 and squares 21 of adhesive are protectively covered with release sheets 22, 23, respectively.

Figure 4:
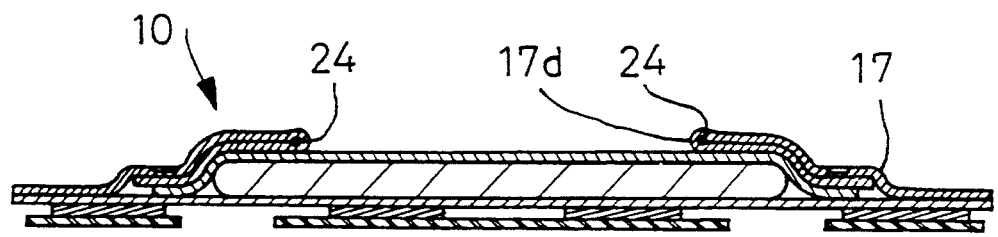
FIG. 4 is an enlarged sectional view showing another embodiment of the napkin as taken along the same line as in FIG. 3.

FIG. 4 shows an alternative embodiment in which the inner side edges 17d of the respective liquid barrier sheets 17 have string-like members 24 wrapped therein so that these inner side edges 17d may bulge. The string-like members 24 are preferably made of soft rubber or foaming plastics.

The manner in which the napkin of the above-mentioned construction is used will be described. First, the release sheets 22 are peeled off to expose the strips 20 of adhesive with which the central area of the napkin is bonded to the inner surface of the crotch zone 25 (FIG. 5) of user's underpants, then the release sheets 23 are peeled off to exposed the squares 21 of adhesive and finally the respective wings 14 are folded and bonded to the outer surface of the crotch zone 25 by said squares 21 of adhesive. With the napkin 10 thus fixed to user's underpants, the inner side edges 17d of the respective liquid barrier sheets 17 are lifted up and the pockets 19 are opened as will be seen in FIG. 5, since the inner areas 17a of said liquid barrier sheets 17 are pulled outward as the wings 14 are folded to the outer surface of the crotch zone 25. Menstrual fluid flowing on the top surface toward the opposite side edges of the napkin 10 is effectively received by said open pockets 19 and thus there is no apprehension that any quantity of menstrual fluid might leak through said opposite side edges and stain the user's underwear. Bottoms of the respective pockets 19 defined by the outer side edges thereof comprise respective outer side edges of the liquid-impermeable backsheet 12 and the liquid barrier sheets 17, respectively, and therefore menstrual fluid once received by the pockets 19 is effectively prevented from leaking through the bottoms of the respective pockets 19.

Industrial Usefulness

As will be appreciated from the foregoing description, the sanitary napkin of the invention allows it to be firmly fixed to the user's underpants so that it may be reliably held thereon even in brisk movement of the user's body. With the napkin of the invention, the liquid barrier sheets defining the flaps which include the wings, respectively, may be bonded to the opposite sides of the napkin itself to complete the product and, accordingly, may be mass-produced at a reasonable cost similar to that for the conventional napkin having the flaps of wing type.

I claim:

1. A sanitary napkin comprising
   (A) a liquid-permeable topsheet (11),
   (B) a liquid-impermeable backsheet (12),
   (C) a liquid absorbent core (13) sandwiched therebetween,
   (D) spaced apart flaps (15) extending outwardly from opposite side edges of the said absorbent core, each of said flaps (15) comprising
      (a) a pair of first flap sections that extends laterally outwardly from the sides of said absorbent core (13), each said first flap section comprising a first outer extension (12a) of said backsheet (12) that is joined to an outer extension (11a) of said topsheet (11),
      (b) a pair of second flap sections in the form of a pair of wings (14) extending outwardly from opposite side edges of said first flap section at about the longitudinally central area of said core (13), each said wing (14) comprising a second outer extension of said backsheet (12) and an overlying liquid barrier backsheet (17),
      said liquid barrier sheet (17) having an inner edge (17d) and an outer edge, said inner edge (17d) overlying said absorbent core (13) and being unbonded to either said first or second flap section, said outer edge being bonded to said second flap section, said barrier sheet (17) also being bonded to said first flap section along a bonding line (18) that is intermediate the said outer and inner edges of said barrier sheet (17) to thereby form a pocket area (19) underneath said barrier sheet (17) when said wing (14) are folded toward each other around the crotch area of the underpants of a user, and
   (E) areas of adhesive (21) on the bottom surface of each wing (14) for bonding each wing to the underpants of a user.

2. The napkin as recited in claim 1, wherein said backsheet (12) is dimensioned wider than said topsheet (11) so that the outer extensions (12b) of said backsheet (12) extend outward beyond outer side edges of the respective outer extensions (11a) of said topsheet (11).

3. The napkin as recited in claim 1, wherein the outer extensions (12b) of said backsheet (12) serving to define said wings (14) are contiguous to the outer sides of the respective outer extensions of said backsheet.

4. The napkin as recited in claim 1, wherein said pockets (19) are formed so as to be deeper in the areas adjacent said wings (14).

5. The napkin as recited in claim 1, wherein the inner areas (17a) of each liquid barrier sheet (7) is turned down and the inner side edge (17d) created by such turning down contains a string member wrapped therein.

* * * * *